United States Patent [19]

Hirth

[11] Patent Number: 5,164,090
[45] Date of Patent: Nov. 17, 1992

[54] PROCESS FOR THE DIRECT CHROMATOGRAPHIC ANALYSIS OF DRUGS AND METABOLITES IN WHOLE BLOOD SAMPLES USING INTERNAL SURFACE REVERSE PHASE TECHNOLOGY

[75] Inventor: Walter W. Hirth, St. Peters, Mo.

[73] Assignee: E. R. Squibb & Sons, Inc., Princeton, N.J.

[21] Appl. No.: 432,439

[22] Filed: Nov. 6, 1989

[51] Int. Cl.$^5$ .............................................. B01D 15/08
[52] U.S. Cl. .................................. 210/635; 210/198.2; 210/656; 435/2; 436/63; 436/57; 436/161; 530/417
[58] Field of Search ................... 210/656, 635, 198.2; 436/63, 57, 161; 435/2; 530/416, 417, 380; 424/11

[56] References Cited

U.S. PATENT DOCUMENTS

| | | | |
|---|---|---|---|
| 3,637,489 | 1/1972 | Haller | 210/656 |
| 4,244,694 | 1/1981 | Farina et al. | 210/198.1 |
| 4,544,485 | 10/1985 | Pinkerton et al. | 210/656 |
| 4,778,600 | 10/1988 | Williams | 210/198.2 |
| 4,828,799 | 5/1989 | Love et al. | 436/63 |

OTHER PUBLICATIONS

Tanai et al., High Performance Liquid chromatographic Drug Analysis by Direct Injection of Whole Blood Samples, *J. Chromatography* 423 (1987), 147–168.
Pinkerton TM, Internal Surface Reversed Phase Separation, Application Note No. 18, Regis Chemical Co., Morton Grove, Ill, Jan. 27, 1987.
Nakagawa et al., Retention Properties of Internal-Surface Reversed-Phase Silica Packing and Recovery of Drugs from Human Plasms, Journal of Chromatography, 420 (1987) 297–311.
T. C. Pinkerton et al., J. Chromatography 367, 412–418 (1986).
S. E. Cook et al., J. Chromatography 368, 233–347 (1986).
I. H. Hagestam et al., Anal. Chem. 57, 1757–1763 (1985).
Pinkerton et al., Biochromatography, vol. 1, No. 2, 96–113 (1986).

*Primary Examiner*—Stanley S. Silverman
*Assistant Examiner*—Neil M. McCarthy
*Attorney, Agent, or Firm*—Timothy J. Gaul

[57] ABSTRACT

Disclosed herein is a process for separation and analysis of free and bound hydrophobic components in whole blood. In this process, whole blood is passed through an internal surface reverse phase material having particles large enough to allow blood cells to pass through. These particles have hydrophobic pores that are small enough to prevent penetration by proteinaceous substances and large enough to allow penetration by free hydrophobic components. Thus, free hydrophobic components are retained by the internal pore surfaces. A non-denaturing solvent is used to wash the whole blood through the material, and a hydrophobic or organic solvent may be separately used to wash the hydrophobic components from the material. This process may be combined with qualitative, quantitative, and selective detection techniques, such as radiolabelling. Effective therapeutic dosages of hydrophobic drugs may be determined by separating the free hydrophobic components by this process and then measuring the levels of the free and bound hydrophobic components to determine the proportion existing in free form.

22 Claims, No Drawings

PROCESS FOR THE DIRECT CHROMATOGRAPHIC ANALYSIS OF DRUGS AND METABOLITES IN WHOLE BLOOD SAMPLES USING INTERNAL SURFACE REVERSE PHASE TECHNOLOGY

FIELD OF THE INVENTION

This invention relates to a process for the separation, analysis and identification of hydrophobic components in whole blood samples.

BACKGROUND OF THE INVENTION

Blood samples often contain important hydrophobic components for which some quantitative or qualitative analysis is desired. Drugs, drug metabolites or degradation products, and lipophilic materials (e.g., cholesterol) are examples of such hydrophobic components found in whole blood.

It is well established that the therapeutic effect of a drug is related to the drug in its free form, not bound to blood proteins or cellular components, and not metabolized. To determine an effective therapeutic dose, therefore, it would be useful to have a process that enables quantitating the amount of a drug in the free form relative to that which is bound to blood components and that which has been metabolized.

In the prior art, high performance liquid chromatography (HPLC) has been used to perform this analysis. However, conventional HPLC columns used for this purpose require cells to be removed prior to analysis to avoid column blockage. When protein accumulation might cause column deterioration, protein separation prior to analysis is also required. Separation of these components (typically through filtration, centrifugation or solvent extraction) is time consuming and so limits rapid, time-dependent studies, during which time a new equilibrium may be established. This limitation is especially significant for such drugs as radiolabelled flow tracers; the biodeposition of these drugs depends upon initial first pass extraction, requiring drug analysis shortly after exposure to biological fluids.

A method described in the literature permits the direct injection of whole blood samples to an HPLC system (Tamai et al., *J. Chromatography*, 423 (1987), 147–168) This method requires the whole blood samples to pass through a pre-column containing a resin with particles greater than 40 μm in diameter, using an aqueous eluent with low salt concentration. This eluent causes the hemolysis of red blood cells, which can alter the equilibrium between free and cell-bound concentrations of the drug and its metabolites.

U.S. Pat. No. 4,544,485 discloses an internal surface reverse phase (ISRP) resin, which is an HPLC chromatographic packing material useful for the analysis of hydrophobic analytes in sera and plasma by direct injection, without column deterioration due to protein accumulation. Such an ISRP resin is comprised of porous particles having hydrophobic inner pore surfaces and hydrophilic outer particle surfaces. To analyze hydrophobic drugs in blood using ISRP resin, however, prior art methods require separation of large cellular components from the sera or plasma before analysis, because the cellular components would mechanically block the chromatographic system. I. H. Hagestam et al., *Anal. Chem.* 57, 1757–1763 (1985); S. E. Cook et al., *J. Chromatography* 368, 233–346 (1986); T. C. Pinkerton et al., *Biochromatography* 1, 98–104 (1986); T. Nakagawa et al., *J. Chromatography* 420, 297–311 (1987); T. C. Pinkerton et al., *J. Chromatography* 367, 412–418 (1986).

Another method using ISRP resin requires dilution of the blood samples with water followed by filtration prior to injection onto the HPLC column "Pinkerton" TM Internal Surface Reversed-Phase Separation, Application Note No. 18 (Regis Chemical Co., 8210 Austin Avenue, Morton Grove, Ill. 60053). These dilution and filtration steps are time consuming. Additionally, the filtration step removes certain whole blood components, thus hindering analysis of whole blood.

A need exists, therefore, for a rapid process for chromatographic separation of hydrophobic components from whole blood that does not require pretreatment of blood samples.

SUMMARY OF THE INVENTION

In accordance with the present invention, a process for separation of free and bound hydrophobic components in whole blood is provided wherein whole blood is passed through an internal surface reverse phase (ISRP) resin and eluted with a nondenaturing solvent, wherein the resin comprises particles having (i) hydrophilic outer surfaces, (ii) pores through the outer surfaces defined by hydrophobic sides, (iii) a particle size large enough to allow blood cells to pass through interstices between the particles, and (iv) a pore size small enough to prevent penetration by proteinaceous substances that may be present in whole blood, which could prevent passage of the blood cells through interstices between the particles forming the resin, and large enough to allow penetration by free hydrophobic components. Thus, the free hydrophobic components in the blood penetrate the pores of the ISRP resin and are retained in proportion to their affinity for the internal surfaces of the resin. The whole blood components (e.g., cells and large proteins) are not retained by the ISRP resin and pass through the resin.

Accordingly, the separation process of this invention has significant advantages over prior art processes. First, it does not require time-consuming pretreatment or post-treatment of blood samples and therefore is more precise than prior art processes. Second, because sera and blood cells remain intact, they may be analyzed after the free hydrophobic components have been removed by the ISRP resin. Third, the process facilitates quantitative analysis of hydrophobic materials in whole blood with only a single chromatographic injection.

In addition, in accordance with the present invention, a process for qualitatively determining the presence of free hydrophobic components is provided. In this process, the free components are separated from the bound components by the above-described process and then identified.

Also provided are processes for selective detection of particular hydrophobic components in free and/or bound form. In these processes, the free and bound hydrophobic components are separated by the above separation process, and the free and/or bound portions are examined to detect the particular hydrophobic components.

Additionally, processes for quantitative measurement of free and/or bound hydrophobic components are provided. In these processes, the free and bound hydrophobic components are separated as described above, and then levels of the free and/or bound hydrophobic components are quantitatively measured. Alternatively, levels of the components in bound form may be determined as the difference between the level in free form and the known total level of the components in the blood sample.

A further process is provided in accordance with this invention for determining the therapeutic dosage of a hydrophobic drug. In this process, the amount of drug needed for therapeutic effect is determined by conventional means, and the amount metabolized or eliminated by the body is determined by conventional means. The free and bound portions of the hydrophobic drug are separated by the above process and the levels of the free and bound portions are quantitatively measured. A proportion of the drug in the free form is determined from the levels so measured.

DETAILED DESCRIPTION OF THE INVENTION

An important aspect of the present invention is the size of the ISRP resin particles. When packed into a column, these particles leave interstices between them, through which flows material to be analyzed. Larger particles, of course, leave larger interstices. The particles employed in carrying out the process o the present invention must be large enough to allow blood cellular components to squeeze through the interstices. On the other hand, the resolving power of the resin decreases as the particles become larger. The particle size, therefore, is preferred to be close to the size at which the blood cells analyzed are just able to squeeze through the interstices.

The following is a chart of the sizes. of the major circulating blood cells in man:

| Cell type | Diameter ($\mu$m) | Concentration (number of cells/mm$^3$) |
| --- | --- | --- |
| Erythrocytes | 5.5–8.5 | male: 5.5 million female: 4.8 million |
| Neutrophils | 10–12 | 4000–5000 |
| Eosinophils | 10–12 | 200 |
| Basophils | 8–10 | 25 |
| Lymphocytes | 7–15 | 1000–3000 |
| Monocytes | 16–22 | 300–400 |
| Platelets | 2–3 | 25,000–500,000 |

(source: Illustrated Physiology (3rd edition). McNaught and Callander, Publ. Churchill Livingstone. 1975. ISBN 0 443 01293 8).

From such data, it has been calculated that a particle size of about 50 to 100 $\mu$m in diameter is preferable for use with human or animal blood, while a size of about 75 $\mu$m is most preferred. It is also preferred that the particles be glass beads.

Each particle has pores large enough to allow penetration of small compounds in blood samples. On the other hand, the pore size must be small enough to inhibit contact between the proteins and the hydrophobic internal pore surfaces. It has been determined that a pore diameter of about 7 to 13 nm is preferable, while a pore diameter of about 10 nm is most preferred.

The process is preferably carried out by packing the ISRP resin into an HPLC column and eluting with a non-denaturing solvent. Optionally, the whole blood may be mixed with a clot-preventing agent (heparin is preferred) before passage through the resin. After injection, the blood cells may be washed from the HPLC column.

The non-denaturing solvent suitable for use herein will be an aqueous, substantially isotonic solution. Phosphate buffered saline (PBS) is a preferred non-denaturing solvent. Other examples of non-denaturing solvents suitable for use herein include, but are not limited to, acetate, citrate and other biological buffers.

The hydrophobic components bound to the pore surfaces may be separately removed from the column (e.g., by elution with a hydrophobic solvent, such as an organic solvent or solvent mixture).

The blood cells and proteins washed from the resin may be retained for further analyses (e.g., for detection of radioactivity). Because blood cells remain intact, the present process allows further separation and quantification (e.g., by hemolysis) of blood cells and those components not bound to the internal surfaces of the ISRP resin particles, such as macromolecules. An ISRP column may be equipped with a column-switching valve, for example, to redirect solvent flow to apparatus for such analyses.

To determine qualitatively the presence of hydrophobic components in whole blood, a whole blood sample may be subjected to the separation process of this invention, and after which the so-separated free hydrophobic components may be identified. Alternatively, the bound hydrophobic components may be identified after the free hydrophobic components have been removed. Hydrophobic components can be separated by conventional chromatography or HPLC (which is preferred), and detected in the chromatographic eluate using conventional chromatographic detection equipment such as ultraviolet detection and the like.

The separation process can also be used for the selective detection of particular hydrophobic components and their degradation products. Particular hydrophobic components of interest may have inherent characteristics that allow them to be detected selectively. After the free and bound hydrophobic moieties are separated, either the removed free components and their degradation products or the remaining whole blood sample can be examined to detect the particular components. Components can be selectively detected by radioactivity-detection, ultraviolet detection, fluorescence detection, and the like. Radioactivity detection is preferred for such selective detection.

For quantitative analysis of hydrophobic components, the present process can be combined, for example, with radioactivity detection, ultraviolet detection (when extinction coefficients are known) and the like. In one alternative method, free radioactive hydrophobic components present in whole blood are separated from the whole blood by the separation process of this invention. One can then measure levels of the hydrophobic components in free or bound form by measuring radioactivity from the whole blood or the separate free hydrophobic components. The specificity of the radioactivity allows detection of hydrophobic materials in a complex sample matrix such as whole blood. As long as a non-denaturing eluant is used for elution of the whole blood components, there is no efficiency loss or pressure increase of either a glass bead ISRP column or a reverse phase analytical column for at least fifty sample injections. The recovery of the radioactive components is generally greater than 95%.

When levels of bound hydrophobic components cannot be directly measured, they can still be quantitatively determined by taking the difference between the levels of free hydrophobic components and the total level of hydrophobic components. The total level of hydrophobic components can be measured by conventional means prior to treating the blood with the hydrophobic components. The levels of the components in free form may be measured as described above using the separation process.

Results from these quantitative analyses may be compared to determine the proportion of hydrophobic materials retained in whole blood. Such comparative data is useful in determining therapeutic dosages for hydrophobic drugs.

The therapeutic dosage of a drug depends on the effective amount of the drug needed to have therapeutic effect and on the drug's bioavailability. Typically, the effective amount is determined by pharmacological studies. When the drug is administered, however, portions of the drug may be (1) metabolized and broken down to an ineffective form, (2) eliminated by the body, or (3) bound to blood cells or plasma proteins and so kept from having therapeutic effect. Thus, in a process for determining a therapeutic dosage of a drug, one must determine an amount needed for therapeutic effect, a proportion eliminated or metabolized to an ineffective form, [1] and a proportion bound to blood cells or plasma proteins. One can determine the portion bound to blood cells and plasma proteins using the process disclosed herein. The amount of the hydrophobic drug in free and bound form can be quantitatively measured as described above and used to calculate the proportion of the drug in free form. The so-calculated proportion in free form may be used in determining a therapeutic dosage.

[1] The metabolized form can sometimes be the active form (e.g., prodrugs). In these cases, the rate of formation of the metabolite rather than the administered form is important in determining the therapeutic dosage. The amount of the pharmaceutically active metabolite in free form in whole blood can also be measured by following the procedure of this invention.

When the protein-bound drug or drug derivative/metabolite cannot be distinguished from the whole blood components by a specific detection mechanism for the drug components, the amount of a free drug and its free metabolites and degradation products may still be determined quantitatively by this process. Since the hydrophobic drug in free form is extracted by the ISRP column, it can be detected by such common analytical techniques as ultraviolet or visible light. Because the concentration of the drug in the free form determines the therapeutic dosage, this method will be useful for determining the concentration of the free drug in whole blood samples without sample pretreatment.

The invention will now be further described by the following working example, which represents a preferred embodiment of the invention. This example is illustrative rather than limiting; the scope of this invention is limited only by the claims appended hereto.

EXAMPLE

The process of the invention for the separation, analysis and identification of hydrophobic components in whole blood was carried out as follows.

(a) Test analyte. The hydrophobic test molecules used to evaluate the performance of the chromatographic system consist of $^{99m}$Tc-BATO (Boronic acid Adducts of Technetium diOxime) complexes as previously described by Treher et al., *J. Labelled Compounds and Radiopharmaceuticals*, 23 (1986), 1118-1120; see also Treher, et al., *Inorganic Chemistry* in press. These compounds are small, radioactive, hydrophobic transition metal complexes having potential use as myocardial and brain perfusion agents.

(b) Test matrix. The test matrices included heparinized samples of freshly drawn rat, guinea pig, and human whole blood.

(c) Liquid chromatographic system. 75 μm glycine phenylalanine phenylalanine (GFF) glass bead ISRP material was packed into a 50×4.6 mm stainless steel HPLC column and used in conjunction with a conventional octylsilane analytical column. The glass bead ISRP column was placed between the injection valve and a 6-port column-switching valve which allows the solvent flow to pass either directly to the radiometric detector or through a 15 cm $C_8$ "Nucleosil" analytical column followed by the radiometric detector.

(d) System test procedure. The appropriate $^{99m}$Tc-BATO complex was mixed with heparinized whole blood. A 20 to 40 uL sample of the whole blood was then taken and injected onto the 50×4.6 mm glass bead GFF ISRP column via an injection valve. The glass bead GFF ISRP column was eluted with 0.1M aqueous ammonium citrate at a pH of 5.0 and a flowrate of 1 ml/minute. The column eluate was directed to the radiometric detector through the use of a 6-port column-switching valve. The radiometric detector is then able to quantitate the amount of hydrophobic $^{99m}$Tc-BATO complex that is associated with the whole blood components. Under these conditions, the unbound $^{99m}$Tc-BATO complex and other hydrophobic metabolites are extracted and retained by the inner pores of the GFF ISRP chromatographic material.

After 1.1 minutes, the column switching valve was placed into a second position, directing the flow to the $C_8$ "Nucleosil " analytical column and to the radiometric detector. After 2.0 minutes, the system flowrate was increased to 1.5 ml/minutes over 0.5 minutes. At 2.0 minutes, a gradient elution to a final solvent composition of 72:28 acetonitrile:0.1M ammonium citrate was begun and continued over 2.0 minutes. This final solvent composition was maintained at a flowrate of 1.5 ml/minute until 12 minutes, when the system was returned to the initial conditions of 100% 0.1M ammonium citrate at a flowrate of 1.0 ml/minute. During this phase of the operation, the hydrophobic $^{99m}$Tc-BATO complex and its metabolites are eluted from the hydrophobic pores of the GFF ISRP chromatographic material and separated by the $C_8$ "Nucleosil" column before detection by the radiometric detector. The radiometric elution profile so developed allows the quantification of the relative amounts of the blood components bound and unbound $^{99m}$Tc-BATO complex.

Table 1 shows the results of analysis of whole human blood samples containing $^{99m}$Tc(DMG)$_3$2MP sampled at various times after mixing. The table provides quantitative data on the amount of hydrophobic material bound to whole blood components, and the amount free in plasma. In addition, rapid analysis of non-bound hydrophobic material provided data on metabolites. The recovery of the total radioactivity for each injection was greater than 95%. Thus, this method can provide a means for quantification of the relative amounts of both the free and whole blood-bound radioactivity, and metabolite profiles of radiolabelled compounds.

TABLE 1

Percentage of components bound to and free in whole human blood following in vitro incubation of $^{99m}$Tc(Cl)DMG-2MP

| Time[1] (Min) | Percentage Bound (Rt = 0.6) | Percentage of free unmodified $^{99m}$Tc | | Percentage of Metabolites | |
|---|---|---|---|---|---|
| | | (Rt = 11.5) | (Rt = 7.6) | (Rt = 8.9) | (Rt = 10.5) |
| 1 | 2.6 | 93.7 | 0.4 | 1.1 | 1.5 |
| 5 | 22.5 | 53.6 | 4.8 | 11.3 | 5.6 |
| 20 | 38.3 | 29.3 | 4.5 | 13.1 | 10.2 |
| 25 | 41.9 | 28.9 | 5.2 | 12.3 | 10.5 |
| 40 | 48.6 | 9.2 | 6.3 | 17.2 | 14.4 |

[1](Incubation time of $^{99m}$Tc(Cl)DMG-2MP in whole blood prior to analysis).
[2]Rt = retention time, in minutes, after start of MPLc run.

What is claimed is:

1. A process for separating free and bound hydrophobic components in whole blood, which consists essentially of passing the whole blood through an internal surface reverse phase resin and eluting the resin with a non-denaturing solvent, wherein the resin comprises particles having:
   (i) hydrophilic outer surfaces;
   (ii) pores through the outer surfaces defined by hydrophobic sides;
   (iii) a particle size sufficient to allow blood cells to pass through interstices between the particles; and
   (iv) a pore size small enough to prevent penetration by proteinaceous substances and large enough to allow penetration by the free hydrophobic components wherein whole blood cells remain intact such that the whole blood cells may be further analyzed for bound hydrophobic components.

2. The process of claim 1, wherein the particle size is about 50 to 100 μm in diameter.

3. The process of claim 1, wherein the particle size is about 75 μm in diameter.

4. The process of claim 1, wherein the pore size is about 7 to 13 nm in diameter.

5. The process of claim 1, wherein the pore size is about 10 nm in diameter.

6. The process of claim 1, wherein the particles comprise glass bead internal surface reverse phase particles.

7. The process of claim 1, further comprising treating the whole blood with a clot-preventing agent before passing it through the resin.

8. The process of claim 7, wherein the clot-preventing agent is heparin.

9. The process of claim 1, wherein the non-denaturing solvent is phosphate buffered saline.

10. A process of qualitatively determining presence of free hydrophobic components in whole blood, which comprises:
    (a) separating free hydrophobic components from the whole blood by the process of claim 1; and
    (b) identifying the so-separated free hydrophobic components.

11. The process of claim 10, wherein the identifying step is carried out with high performance liquid chromatography.

12. A process of selectively detecting presence of particular hydrophobic components and their degradation products in free form in whole blood, which comprises:
    (a) separating free and bound hydrophobic components from the whole blood by the process of claim 1; and
    detecting radioactivity or ultraviolet or fluorescent radiation in the so-separated free hydrophobic components.

13. A process of selectively detecting presence of particular hydrophobic components and their degradation products in bound form in while blood, which comprises:
    (a) separating free hydrophobic components from the whole blood by the process of claim 1; and
    (b) detecting radioactivity or ultraviolet or fluorescent radiation in the whole blood after separating the free hydrophobic components.

14. The process of claim 12, wherein:
    (a) the particular hydrophobic components are radioactive components; and
    (b) the detecting step is carried out by using means for detecting radioactivity.

15. A process of quantitatively measuring levels of hydrophobic components present in free form in whole blood, which comprises:
    (a) separating free hydrophobic components from the whole blood by the process of claim 1; and
    (b) quantitatively measuring levels of the so-separated free hydrophobic components.

16. A process of quantitatively measuring levels of hydrophobic components in bound form in whole blood, which comprises:
    (a) separating free hydrophobic components from the whole blood by the process of claim 1;
    (b) quantitatively measuring levels of the so-separated free hydrophobic components; and
    (c) subtracting the so-measured levels of the free hydrophobic components from a total level of the hydrophobic components present in the whole blood.

17. A process of quantitatively measuring levels of hydrophobic components in bound form in whole blood, which comprises:
    (a) separating free hydrophobic components from the whole blood by the process of claim 1; and
    (b) quantitatively measuring levels of hydrophobic components in the whole blood after the free hydrophobic components have been so-separated from the whole blood.

18. The process of claim 17 wherein the quantitative measuring step is carried out by:
    (i) the hydrophobic components comprise radioactive compounds; and
    (ii) the quantitative measuring step is carried out by measuring radioactivity from the radioactive compounds.

19. In a process for determining the therapeutic dosage of a hydrophobic drug, wherein an amount needed for therapeutic effect is determined and a proportion metabolized or eliminated is determined, the improvement comprising:
 (a) separating free hydrophobic drug components from the whole blood by the process of claim 1;
 (b) quantitatively measuring levels of the so-separated free hydrophobic drug components;
 (c) quantitatively measuring levels of hydrophobic components in the whole blood after the free hydrophobic components have been so-separated from the whole blood;
 (d) determining a proportion of the hydrophobic drug in free or bound form from the levels quantitatively measured in steps (b) and (c).

20. The process of claim 19, wherein:
 (i) the hydrophobic drug components are radioactive; and
 (ii) the quantitative measuring steps (b) and (c) are carried out by measuring radioactivity from the radioactive components.

21. A process for detecting presence of radioactive hydrophobic components in free or bound form in whole blood, which comprises:
 (a) separating free hydrophobic components from whole blood by passing the whole blood through an internal surface reverse phase resin, eluting with a non-denaturing solvent, wherein the resin comprises particles having:
  (i) hydrophilic outer surfaces;
  (ii) pores through the outer surfaces defined by hydrophobic sides;
  (iii) a particle size sufficient to allow blood cells to pass intact through interstices between the particles; and
  (iv) a pore size small enough to prevent penetration by proteinaceous substances and large enough to allow penetration by the free hydrophobic components; and
 (b) detecting radioactivity in the so-separated free hydrophobic components or the whole blood.

22. A process of quantitatively measuring levels of radioactive hydrophobic components in free or bound form in whole blood, which comprises:
 (a) separating free hydrophobic components from whole blood by passing the whole blood through an internal surface reverse phase resin and eluting the resin with a non-denaturing solvent, wherein the resin comprises particles having:
  (i) hydrophilic outer surfaces;
  (ii) pores through the outer surfaces defined by hydrophobic sides;
  (iii) a particle size sufficient to allow blood cells to pass intact through interstices between the particles; and
  (iv) a pore size small enough to prevent penetration by proteinaceous substances and large enough to allow penetration by the free hydrophobic components; and
 (b) measuring radioactivity from the so-separated free hydrophobic components or the whole blood.

* * * * *